United States Patent [19]

Fujioka

[11] Patent Number: 4,650,875

[45] Date of Patent: * Mar. 17, 1987

[54] PREPARATION OF (TRIFLUOROMETHYL)PYRIDINES

[75] Inventor: George S. Fujioka, Walnut Creek, Calif.

[73] Assignee: The Dow Chemical Company, Midland, Mich.

[*] Notice: The portion of the term of this patent subsequent to May 20, 2003 has been disclaimed.

[21] Appl. No.: 492,983

[22] Filed: May 9, 1983

[51] Int. Cl.$^4$ .......................................... C07D 213/26
[52] U.S. Cl. .................................... 546/345; 546/346
[58] Field of Search ............................... 546/346, 345

[56] References Cited

U.S. PATENT DOCUMENTS

| 2,516,402 | 7/1950 | McBee et al. | 546/346 |
| 3,136,822 | 6/1964 | Frainier | 546/346 |
| 3,609,158 | 9/1971 | Torba | 546/346 |
| 3,787,420 | 1/1974 | Torba | 546/346 |
| 3,818,019 | 6/1974 | Rigterink | 546/346 |
| 4,184,041 | 1/1980 | Nishiyama et al. | 546/346 |
| 4,259,496 | 3/1981 | Whittaker | 546/346 |
| 4,266,064 | 5/1981 | Nishiyama et al. | 546/346 |
| 4,288,599 | 9/1981 | Nishiyama et al. | 546/346 |
| 4,590,279 | 5/1986 | Fung et al. | 546/345 |

FOREIGN PATENT DOCUMENTS

| 2045245 | 10/1980 | United Kingdom | 546/346 |
| 0028870 | 5/1981 | United Kingdom | 546/346 |
| 0063872 | 3/1982 | United Kingdom | 546/346 |

Primary Examiner—Richard A. Schwartz
Attorney, Agent, or Firm—Merlin B. Davey

[57] ABSTRACT (Trichloromethyl)pyridine compounds are reacted in the liquid phase with HF in the presence of a metal halide catalyst at superatmospheric pressures to form (trifluoromethyl)pyridine compounds in a high yield.

17 Claims, No Drawings

PREPARATION OF (TRIFLUOROMETHYL)PYRIDINES

BACKGROUND OF INVENTION

The present invention relates to a method of preparing (trifluoromethyl)pyridine compounds and more in particular to a method of preparing chlorinated (trifluoromethyl)pyridine compounds.

Fluorination of (trichloromethyl)pyridine compounds has been carried out by vapor phase fluorination which requires the use of high temperatures. Such vapor phase reactions suffer from disadvantages including, for example, energy costs associated with elevating the temperature of the reactants. Additionally, at the temperature necessary for the vapor phase fluorination reaction, both the starting materials and the end products can be decomposed or converted into undesirable by-products which lead to low conversions and low selectivities to the desired (trifluoromethyl)pyridine products. See, for example, U.S. Pat. Nos. 4,266,064 and 4,288,599.

Another method of preparing (trifluoromethyl)pyridine compounds has been to contact a (trichloromethyl)pyridine compound with antimony trifluorodichloride ($SbF_3Cl_2$). See, for example, U.S. Pat. Nos. 3,136,822; 3,787,420; and 3,818,019. The disadvantages associated with this reaction are, for example, the difficulty in controlling an extremely exothermic reaction, the high cost of antimony trifluorodichloride and the difficulty in recycling the antimony by-product. Thus, it is evident that a more efficient and economical method of preparing (trifluoromethyl)pyridine compounds is desirable.

In U.S. Pat. No. 4,184,041 it is disclosed that (trichloromethyl)pyridines are converted to (trifluoromethyl)pyridines employing HF (at 0°–50° C.) or metal fluorides ($SbF_3$ at 100°–250° C.) as fluorinating agents.

In U.S. Pat. No. 4,259,496, a method is taught for the side-chain fluorination of 3-methylpyridine. In this method, 3-methylpyridine is reacted with HF and chlorine in the liquid phase at an elevated temperature and superatmospheric pressure resulting in the formation of 3-(trifluoromethyl)pyridine, a 3-(dichlorofluoromethyl)pyridine, 3-(difluorochloromethyl)pyridine or derivatives thereof containing one or more chlorine or fluorine atoms as substituents in the pyridine ring.

The present invention differs from the prior known methods of preparing (trifluoromethyl)pyridine compounds by employing superatmospheric pressures when reacting optionally chlorinated (trichloromethyl)-pyridines with HF in the presence of a catalyst whereby the desired (trifluoromethyl)pyridine compounds are produced in a more efficient manner when compared to a non-pressurized reactions.

SUMMARY OF INVENTION

Briefly, in accordance with the present invention, a (trichloromethyl)pyridine compound is reacted under liquid phase conditions with HF in the presence of a metal halide catalyst at a super-atmospheric pressure under conditions sufficient to cause fluorination of the trichloromethyl group to form the desired (trifluoromethyl)pyridine compound. The (trifluoromethyl)pyridine products are useful as intermediates in the synthesis of biologically active compounds, such as, herbicides.

Of particular interest in the practice of this invention is a method of preparing 2,3-dichloro-5-(trifluoromethyl)pyridine and 2-chloro-5-(trifluoromethyl)pyridine, both of which are useful as intermediates in the manufacture of substituted-pyridinyloxy(or thio)phenoxy alkanoic acids and derivatives thereof which are known herbicides.

DETAILED DESCRIPTION OF THE INVENTION

In the practice of the present invention a (trichloromethyl)pyridine compound, HF and a metal halide catalyst are mixed, heated and subjected to superatmospheric pressures.

(Trichloromethyl)pyridine compounds employed as the starting material are unsubstituted or substituted-(trichloromethyl)pyridine compounds containing one or two trichloromethyl groups. The pyridine ring optionally contains other substituents besides the —$CCl_3$ groups, which do not affect the halogen exchange reaction of this invention. Such substituents include, for example, Cl, Br, I or F. Preferred (trichloromethyl)pyridine compounds include $\beta$-(trichloromethyl)-pyridines, such as, 2,3-dichloro-5-(trichloromethyl)-pyridine and 2-chloro-5-(trichloromethyl)pyridine.

Hydrogen fluoride is employed as the fluorinating agent in the present reaction and is present in amounts of at least about 3 molar equivalents per molar equivalent of (trichloromethyl)-pyridine starting material when the starting material is a mono-(trichloromethyl)-pyridine and preferably from about 3 to about 6 molar equivalents. When a bis-(trichloromethyl)pyridine is employed as the starting material then at least about 6 molar equivalents of HF are employed in the reaction and preferably from about 6 to about 12 molar equivalents are employed. Preferably anhydrous HF is employed as the HF source.

Metal halides are employed in catalytic amounts in the present reaction. Suitable metal halides include metal chlorides and metal fluorides. Suitable metal chlorides include $FeCl_3$, $NbCl_5$, $TaCl_5$, $WCl_6$, $SnCl_4$ or mixtures thereof. Suitable metal fluorides include $SbF_3$, $FeF_3$, $AgF$, $KF$, $CrF_2$ or mixtures thereof. The metal halide catalysts are added to the present reaction in catalytic amounts, generally from about 0.1 to about 20 mole percent based on the amount of (trichloromethyl)-pyridine compound starting material present, and preferably from about 1 to about 10 mole percent. Preferred metal halide catalysts include $FeCl_3$ and $FeF_3$.

Also acceptable as a catalyst is a metal halide/phosphorus halide combination. Such a combination is achieved by supplying a phosphorus halide to the reaction mixture in addition to the metal halide catalyst. A preferred phosphorus halide is $PCl_5$.

The present reaction is conducted under liquid phase conditions at superatmospheric pressures, usually at least about 5 psig, preferably at least about 15 psig and up to about 1200 psig, although higher pressures are not detrimental to the present reaction. The present halogen exchange reaction is typically conducted in the presence of agitation sufficient to maintain a thorough contacting of the reactants. While the temperature at which the present reaction is conducted at is not critical, it is usually carried out at temperatures of from about 150° C. to about 250° and preferably from about 170° C. to about 190° C. Below 150° C. the reaction will proceed, but at a slower rate when compared to higher temperatures. Conducting the reaction at temperatures greater than 250° C. results in the accelerated decomposition of (chloromethyl)pyridines which decreases the yield of the desired (trifluoromethyl)pyridines.

In conducting the present reaction the order of addition of the reactants is not critical. Usually the (trichloromethyl)pyridine starting material and liquid HF (anhydrous) are admixed in the reaction vessel and then the catalyst is added. The reactants are thereafter heated and pressurized as described hereinbefore. Generally, the reaction is complete in from about 1 to about 100 hours and will vary depending on factors, such as, temperature, pressure, starting material and catalyst employed. After completion of the reaction, the desired (trifluoromethyl)pyridine compound is separated employing known separatory and purification techniques such as distillation.

In one embodiment of the present invention, 2-chloro-5-(trichloromethyl)pyridine is admixed with at least 3 molar equivalents of anhydrous HF and between 1-10 mole percent metal halide catalyst such as, $FeCl_3$ or $FeF_3$, to form a reaction mixture. The reaction mixture is subjected to a superatmospheric pressure, in the range of from about 5-1,200 psig, at a temperature in the range of from about 150° C.-250° C., until 2-chloro-5-(trifluoromethyl)pyridine is formed in a high yield. The reaction is usually complete in from about 1 to about 100 hours. The 2-chloro-5-(trifluoromethyl)pyridine is then recovered employing known techniques such as distillation.

In a preferred embodiment of the present invention, 2,3-dichloro-5-(trichloromethyl)pyridine is admixed with at least 3 molar equivalents of anhydrous liquid HF and between 1-10 mole percent metal halide catalyst such as, $FeCl_3$ or $FeF_3$, to form a reaction mixture. The reaction mixture is subjected to a superatmospheric pressure, in the range of from about 5-1,200 psig (preferably 15 psig), at a temperature in the range of from about 170° C.-180° C., until 2,3-dichloro-5-(trifluoromethyl)pyridine is formed. The reaction is usually complete in about 25 hours.

The present reaction is characterized by the following chemical equation:

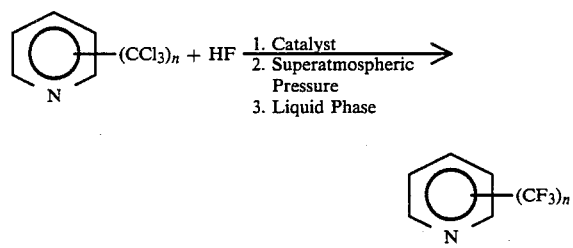

wherein n represents the integers 1 or 2. The above (trichloromethyl)pyridine compound may be further substituted as hereinbefore described, i.e., Cl, Br, I or F. Two preferred reactions are as follows:

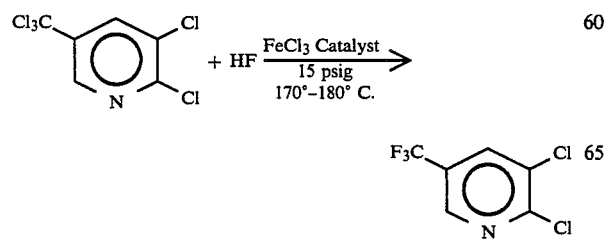

and

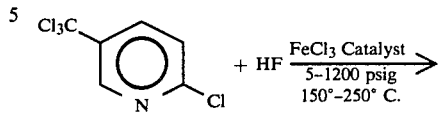

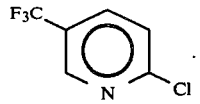

No attempt has been made to balance any of the above chemical equations.

The following examples illustrate the practice of the present invention but should not be construed as limitations upon the overall scope of the same.

EXAMPLE 1

Preparation of 2,3-dichloro-5-(trifluoromethyl)pyridine

A 71 milliliter (ml) Parr bomb (Inconel ®) was charged with 16 grams (g) of 2,3-dichloro-5-(trichloromethyl)pyridine (91% purity), 7 g of anhydrous HF and 0.9 g of anhydrous $FeCl_3$. The bomb was closed and heated to a maximum of 183° C. for 23 hours with rocking agitation. The maximum pressure obtained was 1150 psig. The reactor was allowed to cool to 0° C. in an ice bath and the excess pressure present (about 280 psig) was sparged into water and by analysis found to be HCl. A total of 15.5 g of dark brown liquid was recovered from the bomb and analyzed employing standard gas chromatagraphy procedures. The results of the analysis corresponded to the following molecular distribution:

|  | Percent (area under curve) |
| --- | --- |
| 2,3-dichloro-5-(trifluoromethyl)pyridine | 87.2 |
| 2,3-dichloro-5-(chlorodifluoromethyl)pyridine | 6.0 |
| 3-chloro-2-fluoro-5-(trifluoromethyl)pyridine | 2.5 |
| 2,3-dichloro-5-(dichlorofluoromethyl)pyridine | 1.2 |
| 2,3-dichloro-5-(trichloromethyl)pyridine | 0.8 |
| unidentified | 2.3 |
|  | 100% |

EXAMPLE 2

Preparation of 2,3-dichloro-5-(trifluoromethyl)pyridine

A 300 ml nickel vessel, fitted with a condenser, HF feed port, sampling port, thermocouple and a pressure gauge attached to the HF feed line, was charged with 163.4 g of 2,3-dichloro-5-(trichloromethyl)pyridine (98% purity), 6.4 g of anhydrous $FeCl_3$ and sufficient anhydrous HF to maintain 15 psig pressure at a reactor temperature between 170°-180° C. Excess pressure due to HCl generation was bled out of the top of the reaction vessel through the condenser which was kept at 0° C. After 4 hours at a reaction temperature between 170° C. and 180° C., almost 100% of the starting material had been converted to fluorinated methyl pyridines of the following distribution:

| | Percent (area under curve) |
|---|---|
| 2,3-dichloro-5-(chlorodifluoromethyl)pyridine | 52.7 |
| 3-chloro-2-fluoro-5-(chlorodifluoromethyl)-pyridine | 33.1 |
| 2,3-dichloro-5-(trifluoromethyl)pyridine | 8.4 |
| 3-chloro-2-fluoro-5-(trifluoromethyl)pyridine | 4.9 |
| 2,3-dichloro-5-(dichlorofluoromethyl)pyridine | 0.3 |
| unidentified products | 0.5 |
| | 100% |

EXAMPLE 3

Preparation of 2,3-dichloro-5-(trifluoromethyl)pyridine

Substantially the same procedures employed in Example 1 were repeated except that SnCl$_4$ was employed as the catalyst and HF was added in incremental additions. The results of these variations from Example 1 gave similar product distributions as seen in Example 1.

On repeating the foregoing reactions using other substituted (trichloromethyl)pyridine compounds as starting materials, substantially the same results are obtained whereby the corresponding (trifluoromethyl)-pyridine compounds are produced.

Once prepared, the desired (trifluoromethyl)-pyridine products are separated by distillation from over fluorinated products and any (chlorodifluoromethyl)-, (dichlorofluoromethyl)- or (trichloromethyl)pyridine materials present in the reaction mixture. The ring-fluorinated isomer, i.e., fluoro-(chlorodifluoromethyl)-pyridines such as, 2-fluoro-5-(chlorodifluoromethyl)-pyridine and 3-chloro-2-fluoro-5-(chlorodifluoromethyl)pyridine, which is extremely difficult to separate from the desired (trifluoromethyl)pyridine product is treated with HCl, optionally under pressure, to form the chloro-(chlorodifluoromethyl)pyridine compound which is readily separable from the (trifluoromethyl)-pyridine products. The chloro-(chlorodifluoromethyl)-pyridine is then recycled into the present reaction to form the desired chloro-(trifluoromethyl)pyridine products.

The (trifluoromethyl)pyridine products are employed as starting materials in preparing substituted pyridinyloxy(or thio)phenoxy alkanoic acids and derivatives thereof which are well known herbicides. These herbicides are described in EPO Appl. No. 483 which is incorporated herein by reference.

Starting Materials (Trichloromethyl)pyridines, HF and metal halide catalysts are all well known materials. 2,3-Dichloro-5-(trichloromethyl)pyridine and 2-chloro-5-(trichloromethyl)pyridine are described for example in U.S. Pat. No. 4,184,041 and EPO Patent Application No. 80201077.7, Publication No. 0 028 870.

I claim:

1. A method of preparing a (trifluoromethyl)pyridine compound which comprises contacting in the liquid phase a (trichloromethyl)-pyridine compound with HF in the presence of a catalytic amount of a metal halide catalyst selected from the group consisting of FeCl$_3$, NbCl$_5$, TaCl$_5$, W Cl$_6$, SnCl$_4$ or mixtures thereof, SbF$_3$, FeF$_3$, AgF, KF, CrF$_2$ or mixtures thereof at a superatmospheric pressure of from about 5 to about 1200 psig under conditions sufficient to form said (trifluoromethyl)pyridine compound.

2. The method of claim 1 wherein 2,3-dichloro-5-(trichloromethyl)pyridine is contacted with at least 3 molar equivalents of anhydrous HF at a temperature of from about 150° to about 250° C. whereby 2,3-dichloro-5-(trifluoromethyl)pyridine is formed in a high yield.

3. The method of claim 2 wherein said metal halide catalyst is anhydrous FeCl$_3$.

4. The method of claim 3 wherein said FeCl$_3$ is present in an amount of from about ½ to about 10 mole percent based on the amount of 2,3-dichloro-5-(trichloromethyl)pyridine starting material.

5. The method of claim 4 wherein said pressure is from about 5 to about 1200 psig.

6. The method of claim 5 wherein said pressure is about 15 psig.

7. The method of claim 2 wherein said metal halide catalyst is SnCl$_4$.

8. The method of claim 1 wherein 2-chloro-5-(trichloromethyl)pyridine is contacted with at least 3 molar equivalents of anhydrous HF at a temperature of from about 150° C. to about 250° C. whereby 2-chloro-5-(trifluoromethyl)pyridine is formed in a high yield.

9. The method of claim 8 wherein said metal halide catalyst is anhydrous FeCl$_3$.

10. The method of claim 9 wherein said FeCl$_3$ is present in an amount of from about ½ to about 10 mole percent based on the amount of 2-chloro-5-(trichloromethyl)pyridine starting material.

11. The method of claim 10 wherein said pressure is from about 5 to about 1200 psig.

12. The method of claim 8 wherein said metal halide catalyst is SnCl$_4$.

13. A method of preparing 2,3-dichloro-5-(trifluoromethyl)pyridine which comprises:
   (a) contacting in the liquid phase 2,3-dichloro-5-(trichloromethyl)pyridine with at least 3 molar equivalents of anhydrous HF in the presence of a catalytic amount of a metal halide catalyst to form a reaction mixture;
   (b) heating the reaction mixture to a temperature of from about 170°–190° C.;
   (c) increasing the pressure of the reaction mixture to at least about 15 psig;
   (d) agitating the reaction mixture sufficiently to cause a thorough contacting of the reactants; and
   (e) maintaining the elevated temperature and pressure for a time sufficient to form the desired product in a high yield.

14. The method of claim 13 wherein the metal halide catalyst is present in an amount of from about ½ to about 10 mole percent based on the amount of 2,3-dichloro-5-(trichloromethyl)pyridine.

15. The method of claim 14 wherein the catalyst is FeCl$_3$, FeF$_3$ or SnCl$_4$.

16. The method of claim 15 wherein said pressure is about 15 psig.

17. The method of claim 16 further comprising the step of recovering the desired 2,3-dichloro-5-(trifluoromethyl)pyridine from the reaction mixture.

* * * * *